United States Patent
Pfirmann et al.

(10) Patent No.: US 6,187,952 B1
(45) Date of Patent: Feb. 13, 2001

(54) TWO-STEP PRODUCTION OF 3-CHLORO-4-FLUORO-BENZOYL CHLORIDE BY CHLORINATION

(75) Inventors: Ralf Pfirmann, Grieshiem; Thomas Wessel, Frankfurt, both of (DE)

(73) Assignee: Clariant GmbH, Frankfurt (DE)

( * ) Notice: Under 35 U.S.C. 154(b), the term of this patent shall be extended for 0 days.

(21) Appl. No.: 09/209,963

(22) Filed: Dec. 10, 1998

(30) Foreign Application Priority Data

Dec. 12, 1997 (DE) ................................................ 197 55 298

(51) Int. Cl.$^7$ ...................................................... C07C 51/58

(52) U.S. Cl. .......................................... 562/863; 562/864

(58) Field of Search .................................... 562/864, 863

(56) References Cited

U.S. PATENT DOCUMENTS

| Re. 32,087 | | 2/1986 | Hamprecht et al. . |
| 3,274,242 | * | 9/1966 | Etherington et al. . |
| 4,315,766 | | 2/1982 | Hamprecht et al. . |

FOREIGN PATENT DOCUMENTS

| 1039053 | * | 9/1958 | (DE) . |
| 2325089 | * | 12/1974 | (DE) . |
| 2914915 | | 10/1980 | (DE) . |
| 0903334 A1 | * | 9/1998 | (EP) . |
| 2061257 | * | 5/1981 | (GB) . |

OTHER PUBLICATIONS

"Highly Selective, Novel Analogs of 4–[2–Diphenyl-methoxy)ethyl]1–benzylpiperidine for the Dopamine Transporter: Effect of Different Aromatic Substitutions on Their Affinity and Selectivity," Dutta, Coffey, and Reith, J. Med. Chem. 1997, vol. 40, 35–43.

"The Acetylation of Some Dihalogenobenzenes in Which The Halogen Atoms are Different , " Diep, Buu–Hoï, and Xuong, J. Chem. Soc. [1963], 2784–2787.

"Chlorination of Benzoyl Chloride," E. Hope and G.C. Riley, J. Chem. Soc. [1922]121, pp. 2510–2527.

European Search Report.

Olah G.; J. Chem. Soc. (London); 1957; pt 3, p. 1823–1829.*

Chemical Rubber Company Handbook of Chemistry and Physics; D. Lide Ed.; CRC Press, Boca Raton, vol. 75; 1994.*

Wöhler and Liebig; Justis Liebig's Annalen der Chemie; vol. 3, p. 249, 1832.*

* cited by examiner

*Primary Examiner*—James O. Wilson
*Assistant Examiner*—Robert W. Deemie
(74) *Attorney, Agent, or Firm*—Scott E. Hanf

(57) ABSTRACT

The present invention relates to a process for the preparation of 3-chloro-4-fluorobenzoyl chloride which comprises reacting 4-fluorobenzaldehyde with a chlorinating agent in the presence of a free-radical initiator in the presence or absence of a solvent at from −20 to 200° C. to give 4-fluorobenzoyl chloride, and reacting the 4-fluorobenzoyl chloride with a chlorinating agent in the presence of a chlorination catalyst in the presence or absence of a solvent at from −20 to 200° C. to give 3-chloro-4-fluorobenzoyl chloride.

17 Claims, No Drawings

TWO-STEP PRODUCTION OF 3-CHLORO-4-FLUORO-BENZOYL CHLORIDE BY CHLORINATION

CROSS-REFERENCES TO RELATED APPLICATIONS

The present invention is described in the German priority application No. 197 55 298.6, filed Dec. 12, 1997, which is fully disclosed herein.

The present invention relates to an advantageous process for the preparation of 3-chloro-4-fluorobenzoyl chloride.

BACKGROUND OF THE INVENTION

3-Chloro-4-fluorobenzoyl chloride and its derivatives are important precursors for the preparation of pharmaceuticals and crop-protection compositions (J. Med. Chem. 1997, Vol. 40, 35–43, DE 29 14 915 A1).

3-Chloro-4-fluorobenzoyl chloride is available via a multi-stage synthesis. According to Diep et al., J. Chem. Soc. [1963], 2784–2787, ortho-chlorofluorobenzene is initially reacted with acetyl chloride in the presence of large amounts of aluminum chloride in the presence of carbon disulfide, methylene chloride or tetrachloroethylene, the reaction mixture is decomposed with dilute hydrochloric acid, the organic phase is washed with aqueous sodium hydroxide, then with water, and dried over sodium sulfate, the solvent is evaporated, and the residue is subjected to fractional distillation at reduced pressure. This method gives 3-chloro-4-fluoroacetophenone in a yield of about 80%.

The 3-chloro-4-fluoroacetophenone is then reacted with an aqueous solution of sodium hypobromite, the aqeuous phase is treated with sodium hydrogensulfite and acidified with hydrochloric acid, and the precipitated product is recrystallized from benzene. 3-Chloro-4-fluorobenzoic acid obtained in a yield of 74%.

The 3-chloro-4-fluorobenzoic acid can be reacted with thionyl chloride in the presence of small amounts of pyridine, as in DE 29 14 915, page 20, lines 28 to 35, to prepare the 3-chloro-4-fluorobenzoyl chloride.

This process, which starts from ortho-chlorofluorobenzene, has a number of disadvantages. Firstly, it requires a relatively large number of individual process steps and, secondly, uses a starting material which has relatively poor availability and is expensive, namely ortho-fluorochlorobenzene. Moreover, the Friedel-Crafts acetylation requires the use of large amounts of aluminum chloride and long reaction times (50 hours). In addition, it is carried out in the presence of solvents which create problems, for example carbon disulfide. In the 3-chloro-4-fluorobenzoyl chloride preparation stage, the yield is only 57%. Based on orthofluorochlorobenzene, 3-chloro-4-fluorobenzoyl chloride is obtained in a yield of only 33.7%.

It is known from the publication by E. Hope and G. C. Riley, J. Chem. Soc. [1922] 121, pages 2510–2527 that benzoyl chloride can be reacted with chlorine in the presence of iron(III) chloride to give 3-chlorobenzoyl chloride. As the analysis results on page 2525 show, as well as 76% of monochlorinated compounds, significant amounts of dichlorinated compounds, namely 5%, are formed. The amount of unreacted benzoyl chloride is 13.5%. The 3-chlorobenzoyl chloride is however contaminated with considerable amounts of undesired isomers. Their content is not less than 16.5% (14.5% of 2-chlorobenzoyl chloride and 2% of 4-chlorobenzoyl chloride).

SUMMARY OF THE INVENTION

In view of the situation described above, the object was therefore to provide a process for the preparation of 3-chloro-4-fluorobenzoyl chloride which avoids the disadvantages described above and which is also easy to carry out industrially. In addition, it should make available the desired product in good yields and very good purity.

DESCRIPTION OF THE PREFERRED EMBODIMENTS

This object is achieved by a process for the preparation of 3-chloro-4-fluorobenzoyl chloride. It comprises reacting 4-fluorobenzaldehyde with a chlorinating agent in the presence of a free-radical initiator in the presence or absence of a solvent at from −20 to 200° C. to give 4-fluorobenzoyl chloride, and reacting the 4-fluorobenzoyl chloride with a chlorinating agent in the presence of a chlorination catalyst in the presence or absence of a solvent at from −20 to 200° C. to give 3-chloro-4-fluorobenzoyl chloride.

The advantages of the novel process include the fact that it is possible, firstly, to react a starting material which is available in industrial amounts, and, secondly, it is possible to dispense with the use of a Friedel-Crafts catalyst such as aluminum chloride, which must normally be used in very large amounts. Moreover, the reaction can be carried out with comparatively few working steps having comparatively short reaction times.

It is also very surprising that the novel reaction of 4-fluorobenzoyl chloride with a chlorinating agent to give 3-chloro-4-fluorobenzoyl chloride takes place not only with good yield but also with very high selectivity. In view of the results of the chlorination of benzoyl chloride, not only would a formation of dichlorinated products have been expected, but also appreciable amounts of monochlorinated isomeric 4-fluorobenzoyl chlorides. However, entirely unexpectedly this is not the case. Isomeric 2-chloro-4-fluorobenzoyl chloride is formed only in an amount of about 1% and dichlorofluorobenzoyl chlorides are produced in an amount below 0.5%.

4-Fluorobenzaldehyde and the chlorinating agent are normally used in the molar ratio 1:(0.2 to 1.5), in particular 1:(0.25 to 1), preferably 1:(0.5 to 1).

The chlorinating agent used can be chlorine or a chlorine-releasing agent. Suitable chlorinating agents are chlorine, sulfuryl chloride, thionyl chloride, phosphorus trichloride, phosphorus pentachloride, antimony pentachloride, iodine trichloride, sulfur dichloride, disulfur dichloride, manganese tetrachloride or a mixture thereof.

In particular, 4-fluorobenzaldehyde is reacted with chlorine, sulfuryl chloride, thionyl chloride or a mixture thereof as chlorinating agent.

It has proven particularly favorable to react 4-fluorobenzaldehyde with chlorine as chlorinating agent.

The reaction of 4-fluorobenzaldehyde with the chlorinating agent takes place according to a type of free-radical chlorination, where the presence of a free-radical initiator is beneficial. The free-radical initiator normally used is a peroxide, an azo compound, light having a wavelength of from 200 to 400 nm individually or in combination with one another. It is known that organic peroxides and organic azo compounds dissociate, under the influence of heat and/or light, into free-radicals which initiate the free radical chlorination.

Examples of suitable peroxides or azo compounds are ethyl methyl ketone peroxide, 4,4'-azobis(4-cyanopentanoic acid), 1,1'-azobis-(cyclohexanecarbonitrile), α,α'-azo (isobutyronitrile), α,α'-azodiisobutyroamidine dihydrochloride, tert-butyl hydroperoxide, tert-butyl trimethylsilyl peroxide, cumene hydroperoxide, dibenzoyl peroxide, di-tert-butyl peroxide, lauroyl peroxide and/or tert-butyl perbenzoate, in particular α,α'-azo (isobutyronitrile), tert-butyl hydroperoxide, dibenzoyl peroxide and/or lauroyl peroxide.

Light having a wavelength of from 200 to 400, in particular from 250 to 300 nm, has proven particularly suitable.

In a particularly preferred variant, azobisisobutyronitrile (α,α'-azo(isobutyronitrile)) is used as free-radical initiator.

The free-radical initiator (peroxide and/or azo compound) is normally used in an amount of from 0.1 to 10 mol %, in particular from 0.5 to 5 mol %, preferably from 0.7 to 2 mol %, based on 4-fluorobenzaldehyde.

The reaction of 4-fluorobenzaldehyde with the chlorinating agent takes place in the presence or absence of a solvent. The solvent used may be a chlorinated aliphatic or aromatic hydrocarbon or an aliphatic carboxylic acid having from 1 to 6 carbon atoms. Examples of suitable solvents are 1,2-dichloroethane, methyl chloride, methylene chloride, chloroform, carbon tetrachloride, trichlorobenzene, glacial acetic acid, acetic anhydride, in particular 1,2,4-trichlorobenzene, methyl chloride, glacial acetic acid and acetic anhydride.

In a large number of cases it has proven sufficient to react 4-fluorobenzaldehyde with the chlorinating agent at from 0 to 120° C., in particular at from 40 to 100° C.

In a particular embodiment of the novel process, 4-fluorobenzaldehyde is reacted with the chlorinating agent in the absence of a solvent. This variant can be carried out very easily and is therefore of particular interest.

The 4-fluorobenzoyl chloride formed by the reaction of 4-fluorobenzaldehyde with the chlorinating agent is converted to 3-chloro-4-fluorobenzoyl chloride in a subsequent reaction step.

Normally, the 4-fluorobenzoyl chloride is isolated, for example by distillation, and then reacted with a chlorinating agent to give 3-chloro-4-fluorobenzoyl chloride.

However, it is also possible not to isolate the 4-fluorbenzoyl chloride, but to further process it, for example, in the form in which it is produced in the reaction of 4-fluorobenzaldehyde with the chlorinating agent.

4-Fluorobenzoyl chloride and the chlorinating agent are normally reacted in the molar ratio 1:(0.2 to 1.5), in particular 1:(0.25 to 1), preferably 1:(0.5 to 1).

4-Fluorobenzoyl chloride is reacted with one of the chlorinating agents mentioned above for the reaction of 4-fluorobenzaldehyde, or a mixture thereof. In this connection, it is possible for the chlorinating agents used in the two chlorination steps to be identical or different. The process is straightforward if the same chlorinating agent is used in both chlorination steps.

In a large number of cases, it has proven favorable to react 4-fluorobenzoyl chloride with chlorine, sulfuryl chloride, thionyl chloride or a mixture thereof as chlorinating agent.

In a particular embodiment of the novel process, 4-fluorobenzoyl chloride is reacted with chlorine.

The reaction of the 4-fluorobenzoyl chloride is carried out in the presence of a customary chlorination catalyst. Chlorination catalysts which can be used are, for example, iodine, iodine trichloride, iodine pentachloride, iron, iron(II) chloride, iron(III) chloride, aluminum chloride, disulfur dichloride, antimony trichloride, antimony pentachloride or a mixture thereof.

For a large number of cases it has proven favorable to use iodine, iodine trichloride, iron(III) chloride, disulfur dichloride or a mixture thereof as chlorination catalyst. In a particular embodiment, iron(III) chloride is used as chlorination catalyst.

The chlorination catalyst is used in catalytic amounts, i.e. not in a stoichiometric amount, based on the compound to be converted.

Normally, from 0.001 to 0.05 mol, in particular from 0.002 to 0.03 mol, of chlorination catalyst are used per mole of compound to be chlorinated.

The solvent used is one of the solvents mentioned above for the reaction of 4-chlorobenzaldehyde with the chlorinating agent, or a mixture thereof. The solvents used in the two chlorination steps can be identical or different. The process is particularly straightforward if the solvents used in the two chlorination stages are the same.

In a large number of cases, it has proven sufficient to react 4-fluorobenzoyl chloride with the chlorinating agent at from 30 to 150° C., in particular at from 70 to 130° C.

In a particular embodiment of the novel process, 4-fluorobenzoyl chloride is reacted with the chlorinating agent in the absence of a solvent. This variant can be carried out very easily and is therefore of particular interest.

The process can be carried out batchwise or continuously. It can be carried out at atmospheric pressure, superatmospheric pressure or subatmospheric pressure.

EXAMPLES

The examples below describe the process in more detail without limiting it.

Experimental part

Example 1
Preparation of 4-fluorobenzoyl chloride 10 g of azobis(isobutyronitrile) are added, with stirring, to 620 g of 4-fluorobenzaldehyde (5 mol tel quel, purity >99 GC[a/a]) under protective gas in a 1 l four-necked flask. The mixture is then heated to an internal temperature of 60° C. and, over the course of 7.5 hours, a total of 354 g of chlorine are introduced. The chlorine is added in an amount of 15 liters per hour. Unreacted chlorine is then blown out with nitrogen, and the reaction mixture is cooled to room temperature. The progress of the reaction is monitored using gas-chromatographic analysis (GC).

The product obtained has the following composition:

GC analysis: 10.7% (a/a) of 4-fluorobenzaldehyde 78.8% (a/a) of 4-fluorobenzoyl chloride 8.3% (a/a) of 4,4'-difluorobenzil Selectivity: 88.2%

Conversion: 89.3%

Yield: 78.7% of theory

Product distillation is then carried out under reduced pressure through a packed column (height 120 cm, Sulzer CY packing) at a reflux ratio of 15:1, 4-fluorobenzoyl chloride passing over at 48 mbar at a constant 107° C. The fractionated 4-fluorobenzoyl chloride has a purity of >99.8% (a/a) and is converted in the subsequent stage by means of ring chlorination.

Example 2
Preparation of 3-chloro-4-fluorobenzoyl chloride 50.3 g of iron(III) chloride catalyst are added to 845 g of 4-fluorobenzoyl chloride (5.3 mol tel quel, purity: 99.8% (a/a)) in a chlorination apparatus under protective gas, and the mixture is heated to an internal temperature of 90° C. At this temperature, a total of 370 g of chlorine gas (5.2 mol) are continuously introduced, the chlorine gas stream being adjusted to a value of about 12 liters per hour.

Subsequent GC analysis of the reaction product gives the following result:

23.8% (a/a) of 4-fluorobenzoyl chloride 1.0% (a/a) of 2-chloro-4-fluorobenzoyl chloride 71.8% (a/a) of 3-chloro-4-fluorobenzoyl chloride <0.5% (a/a) of dichlorofluorobenzoyl chloride Selectivity: 94.2%

Conversion: 76.2%

Yield: 71.8% of theory

The reaction mixture is then separated from the iron catalyst by distillation under reduced pressure (24 mbar). The resulting crude distillate is fractionally distilled through a spinning band column, the impurities being removed. The 3-chloro-4-fluorobenzoyl chloride obtained has the following purity (GC analysis):

0.16% (a/a) of 2-chloro-4-fluorobenzoyl chloride 99.6% (a/a) of 3-chloro-4-fluorobenzoyl chloride (b.p.: 104.7° C./21 mbar, melting point: 28° C.)

For additional characterization, the 3-chloro-4-fluorobenzoyl chloride is converted into 3-chloro-4-fluorobenzoic acid.

Preparation of 3-chloro-4-fluorobenzooc acid:

2 g of 3-chloro-4-fluorobenzoyl chloride (purity 99.6% GC [a/a]) are carefully hydrolyzed in 4 g of 50% strength sodium hydroxide solution and 20 g of water at 60° C. The solution is then stirred for a further 2 hours at room temperature. The mixture is then adjusted to a pH of 1 using conc. hydrochloric acid, and the precipitated 3-chloro-4-fluorobenzoic acid is filtered off with suction, washed with water and dried. This gives 1.68 g of 3-chloro-4-fluorobenzoic acid in the form of a white powder.

Yield: 92.8% of theory melting point: 136° C. (lit: 136° C.)

What is claimed is:

1. A process for the preparation of 3-chloro-4-fluorobenzoyl chloride, which comprises reacting 4-fluorobenzaldehyde with a chlorinating agent in the presence of a free-radical initiator in the presence or absence of a solvent at from −20 to 200° C. to give 4-fluorobenzoyl chloride, and reacting the 4-fluorobenzoyl chloride with a chlorinating agent in the presence of a chlorination catalyst in the presence or absence of a solvent at from −20 to 200° C. to give 3-chloro-4-fluorobenzoyl chloride.

2. The process as claimed in claim 1, wherein 4-fluorobenzaldehyde and the chlorinating agent are reacted in the molar ratio 1:(0.2 to 1.5).

3. The process as claimed in claim 1, wherein 4-fluorobenzaldehyde is reacted with chlorine, sulfuryl chloride, thionyl chloride, phosphorus trichloride, phosphorus pentachloride, antimony pentachloride, iodine trichloride, sulfur dichloride, disulfur dichloride, manganese tetrachloride or a mixture thereof as chlorinating agent.

4. The process as claimed in claim 1, wherein 4-fluorobenzaldehyde is reacted with chlorine.

5. The process as claimed in claim 1, wherein a peroxide, an azo compound or light having a wavelength of from 200 to 400 nm are used individually or in combination with one another as free-radical initiator.

6. The process as claimed in claim 1, wherein azobisisobutyronitrile is used as free-radical initiator.

7. The process as claimed in claim 1, wherein the solvent used is a chlorinated, aliphatic or aromatic hydrocarbon or an aliphatic carboxylic acid having from 1 to 6 carbon atoms.

8. The process as claimed in claim 1, wherein 4-fluorobenzaldehyde is reacted with the chlorinating agent in the absence of a solvent.

9. The process as claimed in claim 1, wherein 4-fluorobenzoyl chloride and the chlorinating agent are reacted in the molar ratio 1:(0.2 to 1.5).

10. The process as claimed in claim 1, wherein 4-fluorobenzoyl chloride is reacted with one of the abovementioned chlorinating agents or a mixture thereof.

11. The process as claimed in claim 1, wherein the chlorination catalyst used is iodine, iodine trichloride, iodine pentachloride, iron, iron(II) chloride, iron(III) chloride, aluminum chloride, disulfur dichloride, antimony trichloride, antimony pentachloride or a mixture thereof.

12. The process as claimed in claim 1, wherein the solvent used is one of the abovementioned solvents or a mixture thereof.

13. The process as claimed in claim 1, wherein 4-fluorobenzoyl chloride is reacted with the chlorinating agent in the absence of a solvent.

14. The process as claimed in claim 1, wherein 4-fluorobenzaldehyde and the chlorinating agent are reacted in the molar ratio 1:(0.25 to 1).

15. The process as claimed in claim 1, wherein 4-fluorobenzaldehyde and the chlorinating agent are reacted in the molar ratio 1:(0.5 to 1).

16. The process as claimed in claim 1, wherein 4-fluorobenzoyl chloride and the chlorinating agent are reacted in the molar ratio 1:(0.25 to 1).

17. The process as claimed in claim 1, wherein 4-fluorobenzoyl chloride and the chlorinating agent are reacted in the molar ratio 1:(0.5 to 1).

* * * * *